(12) United States Patent
Graziano

(10) Patent No.: US 11,000,298 B1
(45) Date of Patent: May 11, 2021

(54) MINIMALLY INVASIVE BUNIONECTOMY PROCEDURE USING CHEVRON OSTEOTOMY GUIDE

(71) Applicant: Thomas Graziano, Clifton, NJ (US)

(72) Inventor: Thomas Graziano, Clifton, NJ (US)

( * ) Notice: Subject to any disclaimer, the term of this patent is extended or adjusted under 35 U.S.C. 154(b) by 13 days.

(21) Appl. No.: 16/744,803

(22) Filed: Jan. 16, 2020

(51) Int. Cl.
*A61B 17/17* (2006.01)
*A61B 17/15* (2006.01)
*A61B 17/16* (2006.01)
A61B 17/00 (2006.01)
A61B 17/56 (2006.01)

(52) U.S. Cl.
CPC ........ *A61B 17/1775* (2016.11); *A61B 17/151* (2013.01); *A61B 17/152* (2013.01); *A61B 17/1682* (2013.01); *A61B 17/1796* (2013.01); *A61B 2017/00238* (2013.01); *A61B 2017/564* (2013.01)

(58) Field of Classification Search
CPC . A61B 17/152; A61B 17/151; A61B 17/1775; A61B 17/1682
See application file for complete search history.

(56) References Cited

U.S. PATENT DOCUMENTS

| | | | |
|---|---|---|---|
| 5,843,085 A * | 12/1998 | Graser | A61B 17/151 606/87 |
| 7,972,338 B2 * | 7/2011 | O'Brien | A61B 17/152 606/87 |
| 8,021,367 B2 * | 9/2011 | Bourke | A61B 17/68 606/86 A |
| 8,282,645 B2 * | 10/2012 | Lawrence | A61B 17/15 606/87 |
| 8,388,690 B2 | 3/2013 | Singhatat et al. | |
| 8,545,508 B2 | 10/2013 | Collazo | |

(Continued)

*Primary Examiner* — Christian A Sevilla
(74) *Attorney, Agent, or Firm* — Thomas J. Germinario

(57) ABSTRACT

A chevron osteotomy guide for use in a minimally invasive bunionectomy procedure comprises an oblong base plate having a modified rectangular shape with two parallel longitudinal sides, and having a semi-circular proximal end and a chevron shaped distal end. The chevron shape is isosceles triangular in which a dorsal edge and a plantar edge intersect to form an apex angle that is less than 90 degrees and greater than 60 degrees. In the bunionectomy procedure, the chevron osteotomy guide is attached to the first metatarsal bone using two K wires or pins through proximal and distal apertures in the guide. The proximal aperture is surrounded by two concentric tubular projections which are orthogonal to the plane of the base plate. These projections consist of an inner tubular core, having a circumference that coincides with that of the proximal aperture, and an outer tubular haft, which serves as a handle by which the surgeon adjusts the position of the guide on the first metatarsal bone. Once the osteotomy guide is stabilized on the medial side of the first metatarsal bone, the surgeon uses a sagittal saw sequentially guided along the dorsal edge and then along the plantar edge of the chevron guide, so as complete osteotomies through the dorsal and plantar cortices of the first metatarsal bone. These osteotomies allow the metatarsal head to be translated and pivoted into a position that corrects the patient's bunion condition.

3 Claims, 3 Drawing Sheets

(56) References Cited

U.S. PATENT DOCUMENTS

| | | | |
|---|---|---|---|
| 8,986,353 B2 * | 3/2015 | Johnson | A61B 17/8014 |
| | | | 606/287 |
| 9,044,250 B2 * | 6/2015 | Olsen | A61B 17/16 |
| 9,317,631 B2 * | 4/2016 | Davison | A61B 17/15 |
| 9,427,240 B2 | 8/2016 | Von Zabern et al. | |
| 9,687,250 B2 | 6/2017 | Dayton et al. | |
| 10,039,559 B2 * | 8/2018 | Awtrey | A61B 17/1703 |
| 10,470,779 B2 | 11/2019 | Fallin et al. | |
| 10,786,291 B2 * | 9/2020 | Weiner | A61B 17/151 |
| 2008/0132958 A1 * | 6/2008 | Pech | A61B 17/152 |
| | | | 606/305 |
| 2016/0242791 A1 | 8/2016 | Fallin et al. | |
| 2017/0164989 A1 | 6/2017 | Weiner et al. | |

\* cited by examiner

MINIMALLY INVASIVE BUNIONECTOMY PROCEDURE USING CHEVRON OSTEOTOMY GUIDE

FIELD OF INVENTION

The present invention relates to the general field of osteotomy procedures and more particularly to procedures using osteotomy guides.

BACKGROUND OF THE INVENTION

Medical procedures involving osteotomies often employ devices for guiding the surgical saw in cutting the bones. Bunionectomy procedures require the surgeon to make a precise chevron-shaped cut through the first metatarsal bone. While surgeons typically make this osteotomy configuration in open surgical procedures, the present invention allows the cuts to be made through a minimal incision (0.5-1 inch). This device has the advantage of less dissection/disruption of tissue, which in turn reduces pain and healing time. The cuts in the bone are also made extra-capsular (outside the joint capsule), so that a patient's postoperative recovery of range of motion is faster and less restricted.

As used herein, the terms "proximal" and "distal" refer to the directions on a human foot toward the arch and toward the toes, respectively. The terms "dorsal" and "plantar" refer to the directions on a human foot toward the top of the foot and toward the sole and the foot, respectively. The term "medial" refers to a direction orthogonal to both "dorsal" and "plantar," or toward the side of the foot. As applied to the osteotomy guide, the foregoing definitions apply to the configuration of the guide in use during the bunionectomy procedure described herein.

SUMMARY OF THE INVENTION

The chevron osteotomy guide for use in a minimally invasive bunionectomy procedure comprises an oblong base plate having a modified rectangular shape with two parallel longitudinal sides, and having a semi-circular proximal end and a chevron shaped distal end. The chevron shape is isosceles triangular in which a dorsal edge and a plantar edge intersect to form an apex angle that is less than 90 degrees and greater than 60 degrees. This apex angular range is critical to the ability of the guide to minimize the size of the bunionectomy incision, since chevron angles of 60 degrees or less require open surgical procedures in order to maneuver the surgical saw.

In the bunionectomy procedure, the chevron osteotomy guide is attached to the first metatarsal bone using two K wires or pins through proximal and distal apertures in the guide. The proximal aperture is surrounded by two concentric tubular projections which are orthogonal to the plane of the base plate. These projections consist of an inner tubular core, having a circumference that coincides with that of the proximal aperture, and an outer tubular haft, which serves as a handle by which the surgeon adjusts the position of the guide on the first metatarsal bone.

Once the osteotomy guide is stabilized on the medial side of the first metatarsal bone, the surgeon uses a sagittal saw sequentially guided along the dorsal edge and then along the plantar edge of the chevron guide, so as complete osteotomies through the dorsal and plantar cortices of the first metatarsal bone. These osteotomies allow the metatarsal head to be translated and pivoted into a position that corrects the patient's bunion condition.

The foregoing summarizes the general design features of the present invention. In the following sections, specific embodiments of the present invention will be described in some detail. These specific embodiments are intended to demonstrate the feasibility of implementing the present invention in accordance with the general design features discussed above. Therefore, the detailed descriptions of these embodiments are offered for illustrative and exemplary purposes only, and they are not intended to limit the scope either of the foregoing summary description or of the claims which follow.

DETAILED DESCRIPTION OF THE PREFERRED EMBODIMENT

Figure 1:
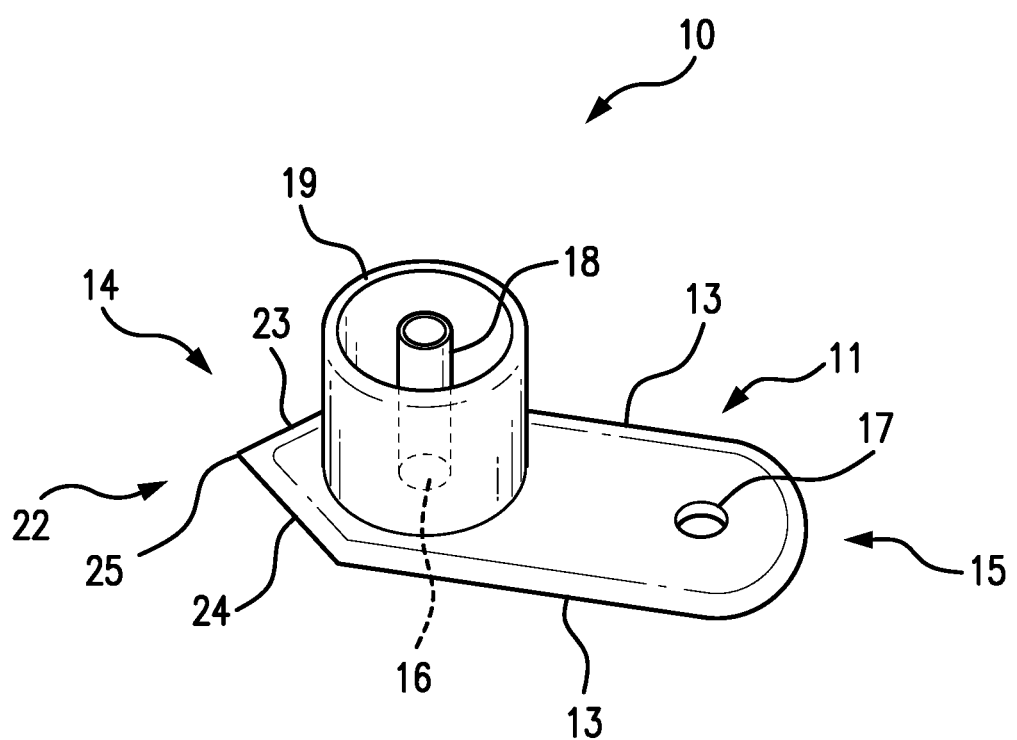
FIG. 1 is a perspective view of the chevron osteotomy guide according to the preferred embodiment of the present invention.
Figure 2:
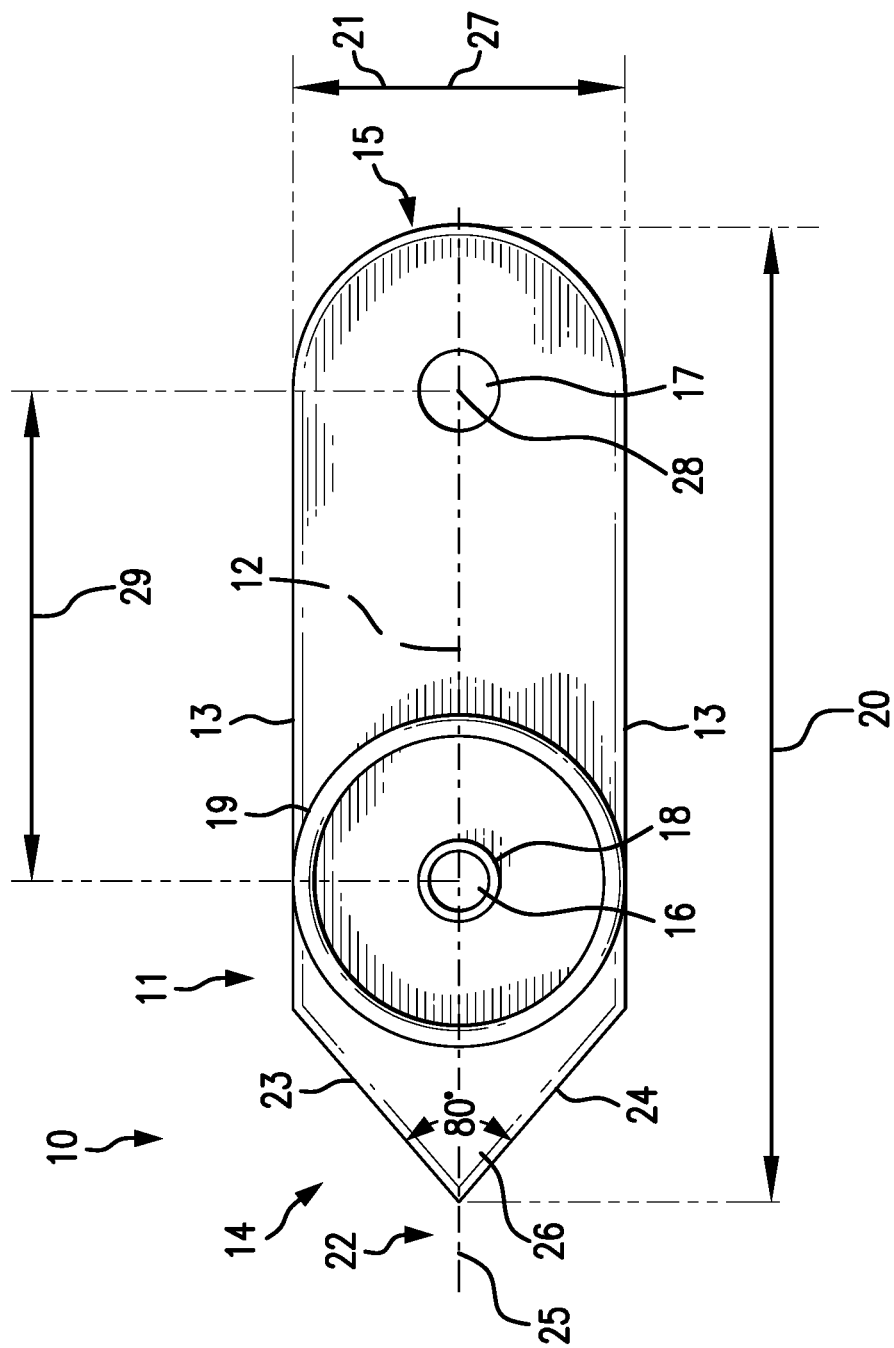
FIG. 2 is a dimensioned plan view of the chevron osteotomy guide according to the preferred embodiment of the present invention.

Referring to FIG. 1 and FIG. 2, an exemplary chevron osteotomy guide, according to the preferred embodiment of the present invention 10, is used in a minimally invasive bunionectomy procedure. The chevron osteotomy guide comprises an oblong base plate 11, having a central longitudinal axis 12, two parallel longitudinal sides 13, a distal end 14, a proximal end 15, a circular distal aperture 16, a circular proximal aperture 17, a tubular core 18, and a tubular haft 19.

While the optimal dimensions of the osteotomy guide 10 are depicted for illustrative purposes in FIG. 2, the base plate has a plate length 20 between ½ inch and 1 inch and a plate width 21 that is ¼ to ½ of the plate length 20. The distal end 14 forms an isosceles triangular chevron 22 having a dorsal edge 23 and a plantar edge 24. As best seen in FIG. 3B, when the osteotomy guide 10 is attached to the medial side of the first metatarsal bone in the bunionectomy procedure, the dorsal edge 23 faces the dorsal (upper) side of the bone, and the plantar edge 24 faces the plantar (lower) side of the bone. The dorsal edge 23 and the plantar edge 24 intersect at the distal apex 25 to form an apex angle 26 that is less than 90° and greater than 60°. Optimally, as shown in FIG. 2, the apex angle 26 is 80°.

The proximal end 15 forms a semi-circular arc with an arc diameter 27 equal to the plate width 21 and an arc center 28 that coincides with the center of the proximal aperture 17. The center of the distal aperture 16 aligns with the center of the proximal aperture 17 along the longitudinal axis 12, and the two centers are separated by an offset distance 29 of approximately ½ the plate length 20, as depicted in FIG. 2.

The distal aperture 16 is concentrically surrounded by two orthogonal projections from the base plate 11, those being the inner tubular core 18 and the outer tubular haft 19. The core circumference at the base of the tubular core 30, where it joins the base plate 11, coincides with the circumference of the distal aperture 16. The longitudinal sides 13 of the base plate 11 are tangential to the haft circumference at the base of the tubular haft 19, where it joins the base plate 11. The diameter of the tubular haft 19 is equal to the plate width 21.

Figure 3A:
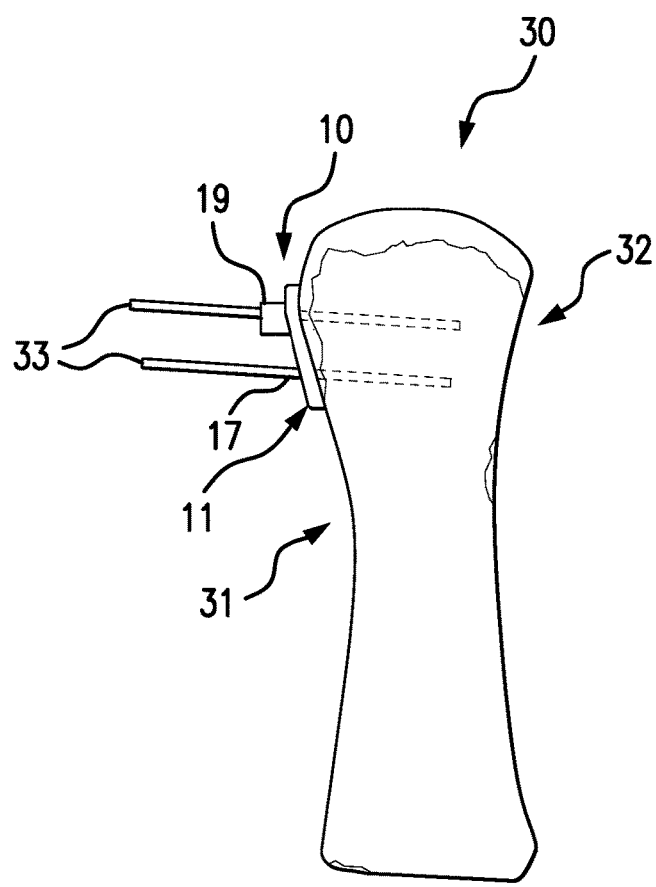
FIG. 3A is a dorsal (top) view of a first metatarsal bone with the chevron osteotomy guide attached to a medial side of the bone, according to the preferred embodiment of the present invention.
Figure 3B:
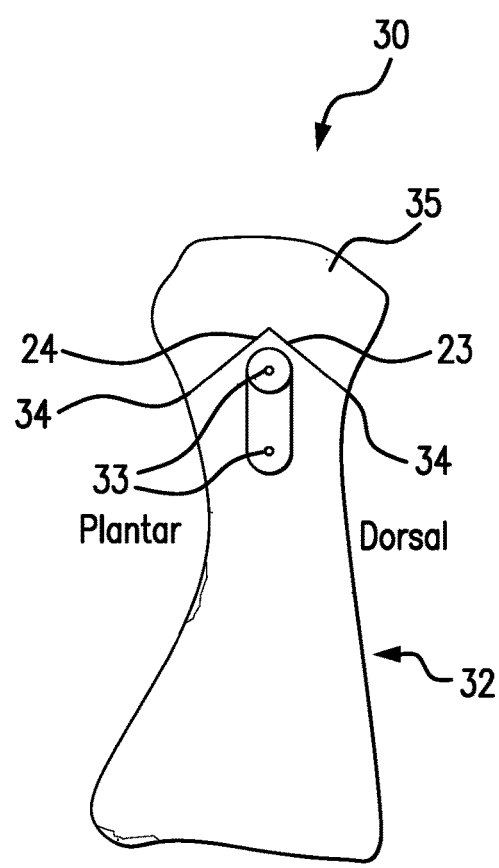
FIG. 3B is a medial (side) view of the first metatarsal bone depicted in FIG. 3A with the attached chevron osteotomy guide and showing the chevron osteotomies (cuts) performed using the guide.

The exemplary minimally invasive bunionectomy procedure 30 is illustrated in FIGS. 3A and 3B. A ½ inch to 1 inch linear incision is made along one of the medial sides 31 of the patient's first metatarsal bone 32. Then the chevron osteotomy guide 10 is inserted into the incision and stabilized against the medial side 31 of the bone 32 using wires or pins 33 through the distal aperture 16 and the proximal aperture 17. The surgeon then uses a sagittal saw to cut through the bone 32, the cut being guided sequentially along the dorsal edge 23 and the plantar edge 24 of the chevron osteotomy guide 10. The osteotomies 34 through the dorsal and plantar cortices of the first metatarsal bone 32 are completed so that a resultant metatarsal head 35 can be translated or pivoted into a corrected bone position, which position can then be fixated using one or more guides and screws.

Although the preferred embodiment of the present invention has been disclosed for illustrative purposes, those skilled in the art will appreciate that many additions, modifications and substitutions are possible, without departing from the scope and spirit of the present invention as defined by the accompanying claims.

What is claimed is:

1. A chevron osteotomy guide device for use in a minimally invasive bunionectomy procedure, the guide device comprising:
    an oblong base plate having a central longitudinal axis, two parallel longitudinal sides, a distal end, a proximal end, a circular distal aperture, a circular proximal aperture, a tubular core, and a tubular haft;
    wherein the base plate has a plate length between ½" and 1" and a plate width which is ¼ to ½ of the plate length;
    wherein the distal end forms an isosceles triangular chevron having a dorsal edge and a plantar edge which intersect at a distal apex forming an apex angle that is less than 90° and greater than 60°;
    wherein the proximal end forms a semi-circular arc having an arc diameter equal to the plate width and having an arc center which coincides with a proximal center of the proximal aperture;
    wherein the distal aperture has a distal circumference and has a distal center, which aligns with the proximal center through the longitudinal axis and which is offset from the proximal center by an offset distance of approximately ½ the plate length;
    wherein the tubular core has a core circumference and has a central core axis, which is orthogonal to the base plate and passes through the distal center;
    wherein the core circumference coincides with the distal circumference; and
    wherein the tubular haft has a central haft axis which is orthogonal to the base plate and which passes through the distal center and which coincides with the core axis, and wherein the tubular haft has a haft circumference to which the two longitudinal sides of the base plate are tangential, and wherein the tubular haft has a haft diameter equal to the plate width.

2. The guide device according to claim 1, wherein the apex angle is approximately 80°.

3. A method of performing the minimally invasive bunionectomy procedure, using the guide device according to claim 1, comprising the following steps:
    (a) making a ½" to 1" linear incision along a medial side of a first metatarsal bone at a distal metaphyseal region of the first metatarsal bone;
    (b) inserting the guide device into the incision;
    (c) inserting wires or pins through the distal aperture and through the proximal aperture of the guide device to stabilize the guide device against the medial side of the first metatarsal bone; and
    (d) using a sagittal saw sequentially guided along the dorsal edge and the plantar edge of the guide device to complete osteotomies through dorsal and plantar cortices of the first metatarsal bone so that a resultant metatarsal head can be translated and/or pivoted into a corrected bone position.

* * * * *